United States Patent [19]
Stern et al.

[11] Patent Number: 5,912,014
[45] Date of Patent: Jun. 15, 1999

[54] ORAL SALMON CALCITONIN PHARMACEUTICAL PRODUCTS

[75] Inventors: William Stern, Tenafly; James P. Gilligan, Union, both of N.J.

[73] Assignee: Unigene Laboratories, Inc., Fairfield, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/616,250

[22] Filed: Mar. 15, 1996

[51] Int. Cl.⁶ .............................. A61K 9/28; A61K 9/30
[52] U.S. Cl. ..................... 424/474; 424/475; 424/477; 424/480; 424/491; 424/457; 424/459; 424/461; 424/426; 514/12
[58] Field of Search ................. 424/426, 474, 424/475, 477, 480, 491, 457, 459, 461; 514/12

[56] References Cited

U.S. PATENT DOCUMENTS

| | | | |
|---|---|---|---|
| 4,604,376 | 8/1986 | Teng | 514/3 |
| 4,708,934 | 11/1987 | Gilligan | 435/68 |
| 4,994,439 | 2/1991 | Longenecker et al. | 514/3 |
| 5,122,376 | 6/1992 | Aliverti et al. | 424/405 |
| 5,206,219 | 4/1993 | Desai | 514/3 |
| 5,310,727 | 5/1994 | Lattanzi et al. | 514/12 |
| 5,350,741 | 9/1994 | Takada | 514/3 |
| 5,447,729 | 9/1995 | Belenduik et al. | 424/440 |
| 5,472,710 | 12/1995 | Klokkers-Bethke et al. | 424/468 |

FOREIGN PATENT DOCUMENTS

| | | |
|---|---|---|
| 0308067 | 8/1988 | European Pat. Off. . |
| 0382403 | 2/1990 | European Pat. Off. . |
| 0517211 | 6/1992 | European Pat. Off. . |
| 9528963 | 4/1994 | WIPO . |

OTHER PUBLICATIONS

"Salmon Calcitonin Versus Human Calcitonin in Paget's Disease of Bone", Current Therapeutic Research, vol. 49, No. 1, Jan. 1991.
Aungst, *J. Pharma. Sci.,* 82(10):979–987 (1993).
Lang, et al., *Am. J. Physiol.,* 251(3 Pt 1):341–48 (1986).
Fix, et al., *Am. J. Physiol.,* 251(3 Pt 1):332–40 (1986).
Ohwaki, et al., *J. Pharm. Sci.,* 76(9):695–99(1987).
Langguth, et al., *Pharm. Research,* 11(4):528 (1994).
Ray, et al., *Biotechnology,* 11:64–70 (1993).
Vector Pharma Ongoing Research "Oral Delivery of Peptides".
Kagatani, et al., *Pharmaceutical Research,* 13(5):739–743 (1996).

*Primary Examiner*—Marian C. Knode
*Assistant Examiner*—Ali R. Salimi
*Attorney, Agent, or Firm*—Ostrolenk, Faber, Gerb & Soffen, LLP

[57] ABSTRACT

Bioavailability of salmon calcitonin to be administered orally is enhanced by a pharmaceutical composition providing targeted release of the peptide to the intestine, together with an absorption enhancer and a sufficient amount of a pH-lowering agent to lower local intestinal pH. Specific concentrations and classes of these agents are disclosed to account for the particular characteristics of salmon calcitonin.

32 Claims, No Drawings

ORAL SALMON CALCITONIN PHARMACEUTICAL PRODUCTS

BACKGROUND OF THE INVENTION

1. Field of the Invention

The present invention relates to oral salmon calcitonin pharmaceuticals, to methods of enhancing bioavailability of orally administered salmon calcitonin, and to methods of treating bone and calcium disorders in humans by orally administering salmon calcitonin in accordance with the invention.

2. Description of the Related Art

Salmon calcitonin is a peptide hormone which decreases uptake of calcium from bone. When used to treat bone-related diseases and calcium disorders (such as osteoporosis, Paget's disease, hypercalcemia of malignancy, and the like), it has the effect of helping maintain bone density. Many types of calcitonin have been isolated (human calcitonin, salmon calcitonin, eel calcitonin, elkatonin, porcine calcitonin, and chicken calcitonin). There is significant structural non-homology among the various calcitonin types. For example, there is 50% percent identity between the amino acids making up human calcitonin and those making up salmon calcitonin.

Salmon calcitonin used in the prior art has usually been administered by injection or by nasal administration. However, these modes of administering the calcitonin are significantly less convenient than, and involve more patient discomfort than, oral administration. Often this inconvenience or discomfort results in substantial patient noncompliance with a treatment regimen. However, the prior art is not believed to have reported an ability to achieve reproducible blood levels of salmon calcitonin when administered orally. This is believed to be because salmon calcitonin lacks sufficient stability in the gastrointestinal tract, and tends to be poorly transported through intestinal walls into the blood.

Proteolytic enzymes of both the stomach and intestines may degrade salmon calcitonin, rendering it inactive before the calcitonin can be absorbed into the bloodstream. Any amount of salmon calcitonin that survives proteolytic degradation by proteases of the stomach (typically having acidic pH optima) is later confronted with proteases of the small intestine and enzymes secreted by the pancreas (typically having neutral to basic pH optima). Other difficulties arising from the oral administration of salmon calcitonin involve the relatively large size of the molecule, and the charge distribution it carries. This may make it more difficult for salmon calcitonin to penetrate the mucus along intestinal walls or to cross the intestinal brush border membrane into the blood. These additional problems may further contribute to the limited bioavailability of salmon calcitonin.

SUMMARY OF THE INVENTION

It is accordingly an object of the present invention to provide a therapeutically effective oral pharmaceutical composition for reliably delivering salmon calcitonin.

It is a further object of the invention to provide therapeutic methods for enhancing the bioavailability of salmon calcitonin.

It is a further object of the invention to provide methods of treating bone-related diseases and calcium disorders by administering salmon calcitonin orally.

In one aspect, the invention provides a pharmaceutical composition for oral delivery of salmon calcitonin comprising (A) a therapeutically effective amount of said salmon calcitonin;
(B) at least one pharmaceutically acceptable pH-lowering agent;
(C) at least one absorption enhancer effective to promote bioavailability of said salmon calcitonin; and
(D) an enteric coating capable of (i) conducting said salmon calcitonin, absorption enhancer and pH lowering agent through a patient's stomach while protecting said salmon calcitonin from degradation by stomach proteases, and (ii) releasing said salmon calcitonin, absorption enhancer and pH lowering agent together into the intestine of said patient;

wherein said pH-lowering agent is present in said pharmaceutical composition in a quantity which, if added to 10 milliliters of a 0.1M aqueous sodium bicarbonate solution, would be sufficient to lower the pH of said solution to no higher than 5.5.

In another aspects the invention provides a method for enhancing the bioavailability of salmon calcitonin delivered orally, said method comprising selectively releasing said salmon calcitonin, together with at least one pH-lowering agent and at least one absorption enhancer, into a patient's intestine following passage of said salmon calcitonin pH lowering agent, and absorption enhancer through the patient's mouth and stomach under protection of an enteric coating which substantially prevents contact between stomach proteases and said salmon calcitonin;

wherein said pH-lowering compound is released by said vehicle into said intestine in an amount which, if added to 10 milliliters of 0.1M aqueous sodium bicarbonate solution, would be sufficient to lower pH of said solution to no higher than 5.5.

The present invention is believed to reduce the likelihood of proteolytic degradation of the salmon calcitonin by simultaneously protecting salmon calcitonin from proteolytic attack by (1) stomach proteases which are typically most active at acidic pH) and (2) intestinal or pancreatic proteases (which are typically most active at basic to neutral pH).

Then the invention is believed to speed the process by which salmon calcitonin crosses the intestinal brush border membrane into the blood, while continuing to protect the salmon calcitonin from proteolytic degradation.

An enteric coating, or the like, protects the peptide active agent from the acid-acting proteases of the stomach. Significant quantities of acid (with which the active agent is intermixed) then reduce the activity of neutral to basic-acting proteases in the intestine (e.g. luminal or digestive protease and proteases of the brush border membrane) by lowering pH out of the optimal activity range of these intestinal proteases. Absorption enhancers of the invention may be used to enhance transport of the peptide agent through intestinal mucous layers, through the brush border membrane and into the blood.

The simultaneous use of absorption enhancers together with a pH-lowering compound, in accordance with the invention, provides a surprisingly synergistic effect on the bioavailability of salmon calcitonin relative to absorption enhancer alone, or pH-lowering compound alone. Compare Table 4 (infra), formulation I (salmon calcitonin alone), Table 3, formulation I (salmon calcitonin and pH-lowering compound) and Table 4, formulation II (salmon calcitonin and absorption enhancer) with Table 4 formulation III (salmon calcitonin, pH-lowering compound, and absorption enhancer).

Other features and advantages of the present invention will become apparent from the following detailed description of the invention.

DETAILED DESCRIPTION OF THE INVENTION

In accordance with the invention, patients in need of treatment with salmon calcitonin are provided with an oral pharmaceutical composition containing the salmon calcitonin in tablet or capsule form of an ordinary size in the pharmaceutical industry. The dosages and frequency of administering the products are discussed in more detail below. Patients who may benefit are any who suffer from calcium disorders or bone diseases. The invention may be used, for example, to treat osteoporosis, Paget's disease, hypercalcemia of malignancy and the like.

Salmon calcitonin is a preferred calcitonin for use in accordance with the invention because it provides a number of advantages over human calcitonin, even though used as a pharmaceutical agent for human patients. Among the advantages provided by utilizing salmon calcitonin instead of human calcitonin for the treatment of human osteoporosis are increased potency, analgesia and increased half-life. Salmon calcitonin is more effective than natural human calcitonin in treatment, since lower dosages are necessary than with human calcitonin. There is substantial non-homology between salmon and human calcitonin, with only 50% identity in the amino acid sequences of the two calcitonins.

The pharmaceutical composition of the invention overcomes a series of different and unrelated natural barriers to bioavailability. Various components of the pharmaceutical compositions act to overcome different barriers by mechanisms appropriate to each, and result in synergistic effects on the bioavailability of salmon calcitonin. As discussed below, inherent physical and chemical properties of salmon calcitonin make certain absorption enhancers more effective than others in boosting bioavailability.

The salmon calcitonin of the invention may be administered orally. In accordance with the invention, proteolytic degradation of the salmon calcitonin by stomach proteases (most of which are active in the acid pH range) and intestinal or pancreatic proteases (most of which are active in the neutral to basic pH range) is reduced. Solubility enhancers aid passage of the peptide active agent through the intestinal epithelial barrier.

Without intending to be bound by theory, it appears that, in accordance with the present invention, the salmon calcitonin is transported through the stomach under the protection of a coating or other appropriate vehicle for substantially preventing contact between the salmon calcitonin and any stomach proteases capable of degrading it. Once the pharmaceutical composition of the invention passes through the stomach and enters the intestinal region where basic to neutral pH predominates, and where proteases tend to have basic to neutral pH optima, the enteric coating or other vehicle releases the salmon calcitonin and acid (in close proximity to each other).

The acid is believed to lower the local intestinal pH, where the active agent has been released to levels below the optimal range for many intestinal proteases. This decrease in pH reduces the proteolytic activity of the intestinal proteases, thus affording protection to the peptide from potential degradation. The activity of these proteases is diminished by the temporarily acidic environment provided by the invention. It is preferred that sufficient acid be provided that local intestinal pH is lowered temporarily to 5.5 or below, especially a range between about 4.0 and 5.5. The sodium bicarbonate test described below (in the section captioned "the pH-Lowering Agent") is indicative of the required acid amount. Preferably, conditions of reduced intestinal pH persist for a time period sufficient to protect the peptide agent from proteolytic degradation until at least some of the peptide agent has had an opportunity to cross the intestinal wall into the bloodstream. Experiments have, in fact, demonstrated $T_{max}$ of 5–15 minutes for salmon calcitonin in the blood when the active components are injected directly into the duodenum, ilium or colon. The absorption enhancers synergistically speed salmon calcitonin into the blood while conditions of reduced proteolytic activity prevail.

The mechanism by which the invention is believed to accomplish the goal of enhanced bioavailability is aided by having active components of the pharmaceutical composition released together as simultaneously as possible. To this end, it is preferred to keep the volume of enteric coating as low as possible consistent with providing protection from stomach proteases. Thus enteric coating is less likely to interfere with salmon calcitonin release, or the release of the other components in close time proximity with the salmon calcitonin. Preferably, the enteric coating adds less than 20% to the weight of the remainder of pharmaceutical composition (i.e., before enteric coating). More preferably, the coating adds between 5 and 15% to the weight of the uncoated ingredients.

The absorption enhancer which may be a solubility enhancer and/or transport enhancer (as described in more detail below) aid transport of the peptide agent from the intestine to the blood, and may speed the process so that it better occurs during the time period of reduced intestinal pH and reduced intestinal proteolytic activity. Many surface active agents may act as both solubility enhancers and uptake enhancers. Again without intending to be bound by theory, it is believed that enhancing solubility provides (1) a more simultaneous release of the active components of the invention into the aqueous portion of the intestine, (2) better solubility of the salmon calcitonin in, and transport through, a mucous layer along the intestinal walls. Once salmon calcitonin reaches the intestinal walls, an uptake enhancer provides better transport through the brush border membrane of the intestine into the blood, via either transcellular or paracellular transport. As discussed in more detail below, many preferred compounds may provide both functions. In those instances, preferred embodiments utilizing both of these functions may do so by adding only one additional compound to the pharmaceutical composition.

Each of the preferred ingredients of the pharmaceutical composition of the invention is separately discussed below. Combinations of multiple pH-lowering agents, or enhancers can be used as well as using just a single pH-lowering agent and single enhancer. Some preferred combinations are discussed below.

The Salmon Calcitonin

The salmon calcitonin preferably comprises from 0.02 to 0.2 percent by weight relative to the total weight of the overall pharmaceutical composition (exclusive of enteric coating). Salmon calcitonin is commercially available (for example, from BACHEM, Torrence, Calif.). Alternatively it may be synthesized by known methods, some of which are discussed briefly below.

Salmon calcitonin precursors may be made by either chemical or recombinant syntheses known in the art. However, the latter is believed significantly more cost effective. Precursors are converted to active salmon calcitonin by amidation reactions that are also known in the art.

For example, enzymatic amidation is described in U.S. Pat. No. 4,708,934 and European Patent Publications 0 308 067 and 0 382 403. Recombinant production is preferred for both the salmon calcitonin precursor and the enzyme that catalyzes the conversion of the precursor to salmon calcitonin. Such recombinant production is discussed in *Biotechnology*, Vol. 11 (1993) pp. 64–70, which further describes a conversion of precursor to recombinant salmon calcitonin product. The recombinant product is identical to natural salmon calcitonin and salmon calcitonin produced using solution and solid phase chemical peptide synthesis.

The production of recombinant salmon calcitonin (rsCT) may proceed, for example, by producing glycine-extended salmon calcitonin precursor in *E. coli* as a soluble fusion protein with glutathione-S-transferase. The glycine-extended precursor has a molecular structure that is identical to active salmon calcitonin except at the C-terminal (where salmon calcitonin terminates -pro-$NH_2$, while the precursor terminates -pro-gly. An $\alpha$-amidating enzyme described in the publications above catalyzes conversion of precursors to salmon calcitonin. That enzyme is preferably recombinantly produced, for example, in Chinese Hamster Ovary (CHO) cells) as described in the Biotechnology article cited above.

The pH-Lowering Agent

The total amount of the pH lowering compound to be administered with each administration of salmon calcitonin should preferably be an amount which, when it is released into the intestine, is sufficient to lower the local intestinal pH substantially below the pH optima for proteases found there. The quantity required will necessarily vary with several factors including the type of compound used (discussed below) and the equivalents of protons provided by a given compound in practice, the amount required to provide good bioavailability for the administered salmon calcitonin is an amount which, when added to a solution of 10 milliliters of 0.1 M sodium bicarbonate, lowers the pH of that sodium bicarbonate solution to no higher than 5.5, and preferably to between 4.0 and 5.5.

The pH-lowering agent of the invention may be any pharmaceutically acceptable compound that is not toxic in the gastrointestinal tract and is capable of either delivering hydrogen ions (a traditional acid) or of inducing higher hydrogen ion content from the local environment. It may also be any combination of such compounds. Examples of compounds inducing higher hydrogen ion content include aluminum chloride and zinc chloride. Pharmaceutically acceptable traditional acids include, but are not limited to acid salts of amino acids (e.g. amino acid hydrochlorides) or derivatives thereof. Examples of these are acid salts of acetylglutamic acid, alanine, arginine, asparigine, aspartic acid, betaine, carnitine, carnosine, citrulline, creatine, glutamic acid, glycine, histidine, hydroxylysine, hydroxyproline, hypotaurine, isoleucine, leucine, lysine, methylhistidine, norleucine, ornithine, phenylalanine, proline, sarcosine, serine, taurine, threonine, tryptophan, tyrosine and valine.

Other examples of useful pH-lowering compounds include carboxylic acids such as acetylsalicylic, acetic, ascorbic, citric, fumaric, glucuronic, glutaric, glyceric, glycocolic, glyoxylic, isocitric, isovaleric, lactic, maleic, oxaloacetic, oxalosuccinic, propionic, pyruvic, succinic, tartaric, valeric, and any combination thereof that achieves the required pH level of no higher than 5.5 in the sodium bicarbonate test discussed above.

Other useful pH-lowering agents that might not usually be called "acids" in the art, but which may nonetheless be useful in accordance with the invention are phosphate esters (e.g., fructose 1, 6 diphosphate, glucose 1, 6 diphosphate, phosphoglyceric acid, and diphosphoglyceric acid). CAROPOL® (Trademark B F Goodrich) and polymers such as polycarbophil may also be used to lower pH.

The Absorption Enhancer

The absorption enhancers are preferably present in a quantity that constitutes from 0.1 to 20.0 percent by weight, relative to the overall weight of the pharmaceutical composition (exclusive of the enteric coating) Preferred absorption enhancers are surface active agents which act both as solubility enhancers and uptake enhancers. Generically speaking, "solubility enhancers" improve the ability of the active components of the invention to be solubilized in either the aqueous environment into which they are originally released or into the lipophilic environment of the mucous layer lining the intestinal walls, or both. "Uptake enhancers" (which are frequently the same surface active agents used as solubility enhancers) are those which facilitate the ease by which peptide agents cross the intestinal wall.

One or more absorption enhancers may perform one function only (e.g., solubility), or one or more absorption enhancers may perform the other function only (e.g., uptake), within the scope of the invention. It is also possible to have a mixture of several compounds some of which provide improved solubility, some of which provide improved uptake and/or some of which perform both. Without intending to be bound by theory, it is believed that uptake enhancers may act by (1) increasing disorder of the hydrophobic region of the membrane exterior of intestinal cells, allowing for increased transcellular transport; or (2) leaching membrane proteins resulting in increased transcellular transport; or (3) widening pore radius between cells for increased paracellular transport.

Surface active agents are believed to be useful both as solubility enhancers and as uptake enhancers. For example, detergents are useful in (1) solubilizing all of the active components quickly into the aqueous environment where they are originally released, (2) enhancing lipophilicity of the components of the invention, especially the peptide active agent aiding its passage into and through the intestinal mucus, (3) enhancing the ability of the normally polar peptide active agent to cross the epithelial barrier of the brush border membrane; and (4) increasing transcellular or paracellular transport as described above.

When surface active agents are used as the absorption enhancers, it is preferred that they be free flowing powders for facilitating the mixing and loading of capsules during the manufacturing process. Because of inherent characteristics of salmon calcitonin (e.g., its isoelectric point, molecular weight, amino acid composition, etc.) certain surface active agents are preferred. Indeed, some can undesireably interact with the charged portions of salmon calcitonin and prevent its absorption, thus undesireably resulting in decreased bioavailability. It is therefore preferred, when trying to increase the bioavailability of salmon calcitonin, that any surface active agent used as an absorption enhancer be selected from the group consisting of (i) anionic surface active agents that are cholesterol derivatives (e.g., bile acids), (ii) cationic surface agents (e.g., acylcarnitines, phospholipids and the like), (iii) nonionic surface active agents, and (iv) mixtures of anionic surface active agents (especially those having linear hydrocarbon regions) together with negative charge neutralizers for said salmon calcitonin.

Negative charge neutralizers include but are not limited to acylcarnitines, cetyl pyridinium chloride, and the like. It is also preferred that the absorption enhancer be soluble at acid pH, particularly in the 3.0 to 5.0 range. One especially preferred combination mixes cationic surface active agents with anionic surface active agents that are cholesterol derivatives, both of which are soluble at acid pH. A particularly preferred combination is an acid soluble bile acid together with a cationic surface active agent. When a single absorption enhancer is used alone, it is preferred that it be a cationic surface active agent. It is the intent of these preferences to avoid interactions with salmon calcitonin that interfere with absorption of salmon calcitonin into the blood.

To reduce the likelihood of side effects, preferred detergents are either biodegradable or reabsorbable (e.g. bile acids, phospholipids, and/or acylcarnitines). Acylcarnitines are believed particularly useful in enhancing paracellular transport When a bile acid (or another anionic detergent lacking linear hydrocarbons) is used in combination with a cationic detergent, salmon calcitonin is better transported both to and through the intestinal wall.

Preferred absorption enhancers include: (a) salicylates such as sodium salicylate, 3-methoxysalicylate, 5-methoxysalicylate and homovanilate; (b) bile acids such as taurocholic, tauorodeoxycholic, deoxycholic, cholic, glycholic, lithocholate, chenodeoxycholic, ursodeoxycholic, ursocholic, dehydrocholic, fusidic, etc.; (c) non-ionic surfactants such as polyoxyethylene ethers (e.g. Brij 36T, Brij 52, Brij 56, Brij 76, Brij 96, Texaphor A6, Texaphor A14, Texaphor A60 etc.), p-t-octyl phenol poloxyethelyenes (Triton X-45, Triton X-100, Triton X-114, Triton X-305 etc.) nonylphenoxypoloxyethylenes (e.g. Igepal CO series), polyoxyethylene sorbitan esters (e.g. Tween-20, Tween-80 etc.); (d) anionic surfactants such as dioctyl sodium sulfosuccinate; (e) lyso-phospholipids such as lysolecithin and lyso-phosphatidylethanolamine; (f) acylcarnitines, acylcholines and acyl amino acids such as lauroylcarnitine, myristoylcarnitine, palmitoylcarnitine, lauroylcholine, myristoylcholine, palmitoylcholine, hexadecahoyllysine, N-acylphenylalanine, N-acylglycine etc.; g) water soluble phospholipids such as diheptanoylphosphatidylcholine, dioctylphosphatidylcholine etc.; (h) medium-chain glycerides which are mixtures of mono-, di- and triglycerides containing medium-chain-length fatty acids (caprylic, capric and lauric acids); (i) ethylenediaminetetraacetic acid; (j) cationic surfactants such as cetylpyridinium chloride; (k) fatty acid derivatives of polyethylene glycol such as Labrasol, Labrafac, etc.; and (l) alkylsaccharides or acyl saccharides such as lauryl maltoside, lauryl sucrose, myristoyl sucrose, palmitoyl sucrose, etc.

In some preferred embodiments, cationic detergents are included to provide solubility enhancement by another mechanism. In particular, prevents the binding of salmon calcitonin to mucus. Preferred cationic ion exchange agents include protamine chloride or any other polycation.

Other Optional Ingredients

In some preferred embodiments, a protein (such as albumin, casein, soy protein, other animal or vegetable proteins and the like) is included to reduce non-specific adsorption (e.g., binding of salmon calcitonin to the intestinal mucus barrier, thereby lowering the necessary concentration of expensive salmon calcitonin. When added, the protein is preferably from 1.0 to 10.0 percent by weight relative to the weight of the overall pharmaceutical composition (exclusive of enteric coating).

All pharmaceutical compositions of the invention may optionally also include common pharmaceutical diluents, glycants, lubricants, gelatin capsules, preservatives, colorants and the like in their usual known sizes and amounts. In some embodiments peptides that may act as substrates for intestinal proteases are added (preferably from 1.0 to 10.0 percent by eight relative to the weight of the overall pharmaceutical composition (exclusive of enteric coating).

The Carrier or Vehicle

Any carrier or vehicle that protects the salmon calcitonin from stomach proteases and which releases active components of the invention in the intestine is suitable. Many enteric coatings are known in the art, and are useful in accordance with the invention. Examples include cellulose acetate phthalate, hydroxypropylmethylethylcellulose succinate, hydroxypropylmethylcellulose phthalate, carboxylmethylethylcellulose and methacrylic acid-methyl methacrylate copolymer.

Suitable enteric coatings for protecting the peptide agent from stomach proteases may be applied to capsules, with the remaining active components of the invention loaded within the capsule. In other embodiments, enteric coating is coated on the outside of a tablet or coated on the outer surface of particles of active components which are then pressed into tablet form, or loaded into a capsule, which is itself preferably enteric coated. In other embodiments, active components of the invention are included in a sufficiently viscous protective syrup to permit protected passage of the active components through the stomach. The term "active components" includes all compounds pertinent to the invention (for example, salmon calcitonin, absorption enhancers such as solubility and/or uptake enhancer(s) and pH-lowering compound(s).

It is very desirable that all of the active components be released from the carrier or vehicle, and solubilized in the intestinal environment as simultaneously as possible. It is preferred that the vehicle or carrier release the active components in the small intestine where uptake enhancers that increase transcellular or paracellular transport are less likely to cause undesirable side effects than if the same uptake enhancers were later released in the colon. It is emphasized, however, that the present invention is believed effective in the colon as well as in the small intestine. Numerous vehicles or carriers, in addition to the ones discussed above, are known in the art. It is desirable (especially in optimizing how simultaneously the components of the invention are released) to keep the amount of enteric coating low. Preferably, the enteric coating adds no more than 20% to the weight of the remainder of pharmaceutical composition (exclusive of enteric coating) More preferably, it adds from 5 to 15 percent to the weight of the uncoated composition.

A preferred pharmaceutical composition of the invention includes a size 0 gelatin capsule filled with 0.25 mg. of salmon calcitonin, 400 mg. of granular citric acid (available for example from Archer Daniels Midland Corp.), 100 mg. of taurodeoxycholic acid (available for example from SIGMA), 100 mg. lauroylcarnitine (SIGMA), 40 mg. albumin and 10 mg. silica (as a dessicant).

All of the foregoing ingredients are for eventual insertion into the gelatine capsule, and are powders which may be added to a blender in any order. Thereafter, the blender is run for about five minutes until the powders are thoroughly intermixed. Then the mixed powders are loaded into the large end of the gelatine capsules. The other end of the capsule is then added, and the capsule snapped shut. 500 or more such capsules may be added to a coating device (e.g., Vector LDCS 20/30 Laboratory Development Coating System (available from Vector Corp., Marion, Iowa)).

An enteric coating solution is made as follows. Weigh 500 grams of EUDRAGIT L30 D-55 (a methacrylic acid copolymer with methacylic acid methyl ester, an enteric coating available from RÖHM Tech Inc., Maidan, Mass.). Add 411 grams distilled water, 15 grams triethyl citrate and 38 grams talc. This amount of coating will be sufficient to coat about 500 size 0 capsules.

The capsules are weighed and placed into the drum of the coating machine. The machine is turned on to rotate the drum (now containing capsules) at 24–28 rpm. The temperature of inlet sprayer is preferably about 45° C. Exhaust temperatures are preferably about 30° C. Uncoated capsule temperature is preferably about 25° C. Air flow is about 38 cubic feet per minute.

A tube from the machine is then inserted into the coating solution prepared as discussed above. The pump is then turned on for feeding solution into the coating device. Coating then proceeds automatically. The machine can be stopped at any time to weigh capsules to determine if the coating amount is sufficient. Usually coating is allowed to proceed for 30 to 60 minutes. The pump is then turned off for about five minutes while the machine is still running to help dry the coated capsules. The machine can then be turned of f The capsule coating is then complete, although it is recommended that the capsules be air dried for about two days.

Because of the enhanced bioavailability provided by the present invention, the concentration of expensive salmon calcitonin in the pharmaceutical preparation of the invention may be kept relatively low.

Treatment of Patients

Treatment of osteoporosis with salmon calcitonin proceeds best with periodic administration Salmon calcitonin is metabolized quickly with a half-life of only 20–40 minutes following subcutaneous administration in man. However, its beneficial effect on osteoclasts is much longer lasting, and may last for more than 24 hours notwithstanding rapid decrease in blood levels. There is usually no-detectable blood levels more than two hours after injection of salmon calcitonin at usual dosages. Accordingly periodic administration of one dose about 5 days per week is preferred. Subcutaneous administration of salmon calcitonin (100 International units) has frequently resulted in peak serum concentration of about 200 picograms per milliliter. Nasally administered salmon calcitonin (200 International units) has proven effective against osteoporosis at peak levels as low as 10 picograms per milliliter. Some patients report some gastrointestinal distress at high peak levels (e.g. at 200 picograms per milliliter). Accordingly, it is preferred that serum salmon calcitonin peak between 10 and 150 picograms per milliliter, more preferably between 10 and 50 picograms per milliliter. The serum levels may be measured by radioimmunoassay techniques known in the art. The attending physician may monitor patient response, salmon calcitonin blood levels, or surrogate markers of bone disease (such as urinary pyridinoline or deoxypyridinoline), especially during the beginning of treatment. He may then alter the dosage somewhat to account for individual patient metabolism and response.

The bioavailability achievable in accordance with the present invention permits oral delivery of salmon calcitonin into the blood at the above-identified preferred concentration levels while using only 100–1000 micrograms of salmon calcitonin per capsule, preferably 100–400 micrograms, especially between 100 and 200 micrograms.

It is preferred that a single capsule be used at each administration because a single capsule best provides simultaneous release of the polypeptide, pH-lowering agent and absorption enhancers. This is highly desirable because the acid is best able to reduce undesirable proteolytic attack on the polypeptide when the acid is released in close time proximity to release of the polypeptide. Near simultaneous release is best achieved by administering all components of the invention as a single pill or capsule. However, the invention also includes dividing the required amount of acid and enhancers among two or more capsules which may be administered together such that they together provide the necessary amount of all ingredients.

Set forth below are a series of tables showing the effect on bioavailability caused by varying certain parameters.

TABLE 1

Effect of Buffer pH on the Absorption of Salmon Calcitonin from the Duodenum of the Rat

| | Formulation | pH* | Peak Plasma Calcitonin ng/ml | Absolute Bioavailability percent |
|---|---|---|---|---|
| I. | Citrate/Citric acid (77 mg) Calcitonin (0.1 mg) | 5 | 0.4 | 0.02 |
| II. | Citrate/Citric acid (77 mg) Calcitonin (0.1 mg) | 4 | 1.9 | 0.10 |
| III. | Citrate/Citric acid (77 mg) Calcitonin (0.1 mg) | 3 | 4.1 | 0.64 |
| IV. | Citrate/Citric acid (77 mg) Calcitonin (0.1 mg) | 2 | 4.8 | 0.69 |

*buffer pH

Method

Female Wistar rats (250–275 g) (n=3 for each formulation) were anesthetized with ketamine and xylazine prior to the insertion of a cannula in the carotid artery. The cannula was fitted to a three way valve through which blood was sampled and replaced with physiological saline. A midline incision was made in the abdominal cavity and 0.5 ml of formulation was injected directly into the exposed duodenum. The pH of the formulation was adjusted by mixing varying amounts of equal molar concentrations of citric acid and sodium citrate. Blood (0.5 ml) was collected before and at 5, 15, 30, 60 and 120 minutes after the administration of the formulation. Samples of blood were centrifuged for 10 minutes at 2600 g and the resulting plasma supernatant was stored as −20° C. The concentration of calcitonin in plasma was determined by a competitive radioimmunoassay. The absolute bioavailability (i e., relative to an intravenous dose of calcitonin) was calculated from the areas under the curve obtained from plots of the plasma concentration of calcitonin as a function of time.

Results and Discussion

When the pH of the buffer was reduced from 5 (formulation I) to 4 (formulation II) the absolute bioavailability increased 5 fold from 0.02% to 0.1%. When the pH was reduced to 3 (formulation III) the absolute bioavailability increased an additional 6.4 fold. There was very little increase in the bioavailability of calcitonin when the pH was reduced to 2. The overall bioavailability of calcitonin increased 32 fold when the pH of the buffer was reduced from 5 to 3.

TABLE 2

Effect of Citric Acid Concentration on the
Bioavailability of Salmon Calcitonin from the Duodenum of the Rat

| | Formulation | Peak Plasma Calcitonin ng/ml | Absolute Bioavailability percent |
|---|---|---|---|
| I. | Citric acid (9.6 mg) Taurodeoxycholic acid (5 mg) Mannitol (22 mg) Calcitonin (0.1 mg) | 3.65 | 0.25 |
| II. | Citric acid (48 mg) Taurodeoxycholic acid (5 mg) Mannitol (22 mg) Calcitonin (0.1 mg) | 17.44 | 2.43 |

Method

Formulations consisting of a constant amount of taurodeoxycholic acid and 2 different amounts of citric acid in a total volume of 0.5 ml were administered into the duodenums of anesthetized rats as described in the legend to Table 1. Mannitol was included in formulations as a marker to measure paracellular transport. Samples of blood were removed at various times and analyzed for calcitonin as described previously.

Results and Discussion

The bioavailability of salmon calcitonin administered in the presence of 9.6 mg citric acid (I) was 0.25%, whereas in the presence of 48 mg citric acid (II) the bioavailability was 2.43%. In the presence of a fixed amount of taurodeoxycholic acid the bioavailability of salmon calcitonin increased nearly 10 fold when the amount of citric acid in the formulation was increased only 5 fold.

TABLE 3

Effect of Enhancers in the Presence of Citric Acid
on the Absorption of Salmon Calcitonin from the Duodenum of the Rat

| | Formulation | Peak Plasma Calcitonin ng/ml | Absolute Bioavailability percent |
|---|---|---|---|
| I. | Citric acid (77 mg) Calcitonin (0.1 mg) | 4.8 | 0.69 |
| II. | Citric acid (48 mg) Taurodeoxycholic acid (5 mg) Calcitonin (0.1 mg) | 26.59 | 3.03 |
| III. | Citric acid (48 mg) Taurodeoxycholic acid (5 mg) Cetylpyridinium chloride (5 mg) Calcitonin (0.1 mg) | 36.48 | 4.54 |
| IV. | Citric acid (48 mg) Tween-20 (5 mg) Calcitonin (0.1 mg) | 15.50 | 3.10 |
| V. | Citric acid (48 mg) Sucrose ester-15 (5 mg) Mannitol (22 mg) Calcitonin (0.1 mg) | 38.93 | 5.83 |
| VI. | Citric acid (48 mg) Lauroylcarnitine chloride (5 mg) Calcitonin (0.1 mg) | 38.89 | 4.53 |
| VII. | Citric acid (48 mg) Diheptanoylphosphatidylcholine (5 mg) Calcitonin (0.1 mg) | 20.93 | 2.97 |

Method

Formulations consisting of citric acid, calcitonin and various classes of enhancers in a total volume of 0.5 ml were administered into the duodenums of anesthetized rats as described in the legend to Table 1. Mannitol was included in formulation V as a marker to measure paracellular transport. Samples of blood were removed at various times and analyzed for calcitonin as described previously.

Results and Discussion

In the absence of an enhancer, the absolute bioavailability of calcitonin was 0.69%. The inclusion of a water soluble phospholipid (formulation VII) increased the bioavailability 4.3 fold to 2.97%. The most effective enhancer was the sugar ester class (formulation V) in which the calcitonin bioavailability was 5.83%. The use of a mixture of bile acid and a cationic detergent (formulation III) a non-ionic detergent (formulation IV) and an acylcarnitine (formulation VI) resulted in intermediate bioavailabilities ranging from 3.03% to 4.53%. The differences in the bioavailabilities of calcitonin in the presence of various classes of enhancers are minor compared to that observed when only citric acid and no enhancer is present in the formulation.

TABLE 4

Effect of Lauroylcarnitine in the Presence of Various Additives
on the Absorption of Salmon Calcitonin from the Duodenum of the Rat

| | Formulation | Peak Plasma Calcitonin ng/ml | Absolute Bioavailability percent |
|---|---|---|---|
| I. | Calcitonin (1 mg) | 9.44 | 0.096 |
| II. | Lauroylcarnitine chloride (5 mg) Calcitonin (0.1 mg) | 2.27 | 0.17 |
| III. | Laurylcarnitine chloride (5 mg) Citric acid (48 mg) Calcitonin (0.1 mg) | 38.89 | 4.53 |
| IV. | Laurylcarnitine chloride (1 mg) Citric acid (48 mg) Calcitonin (0.1 mg) | 27.72 | 4.81 |
| V. | Laurylcarnitine chloride (5 mg) Diheptanoylphosphatidylcholine (5 mg) Citric acid (48 mg) Calcitonin (0.1 mg) | 44.89 | 6.45 |
| VI. | Lauroylcarnitine chloride (5 mg) Bovine Serum Albumin (25 mg) Calcitonin (0.1 mg) | 4.58 | 0.42 |

Method

Formulations consisting of lauroylcarnitine, calcitonin and various other compounds in a total volume of 0.5 ml were administered into the duodenums of anesthetized rats as described in the legend to Table 1. Samples of blood were removed at various times and analyzed for calcitonin as described previously.

Results and Discussion

In the absence of citric acid or any enhancer (formulation I), the absolute bioavailability of calcitonin was 0.096%. In the presence of 5 mg lauroylcarnitine chloride (formulation II), the bioavailability increased 1.8 fold to 0.17%. When citric acid was included with lauroylcarnitine (formulation III), the bioavailability increased an additional 27 fold to 4.53%. A 5 fold reduction in the amount of lauroylcarnitine but not citric acid (formulation IV), did not significantly reduce the bioavailability of salmon calcitonin. The inclusion of 5 mg diheptanoylphosphatidylcholine to formulation III to produce formulation V increased the bioavailability slightly (1.4 fold). The substitution of 25 mg bovine serum albumin for citric acid (formulation VI) reduced the bioavailability from 4.53% (formulation III) to 0.42%. These results taken together show the synergistic effect between a pH-lowering substance like citric acid and an enhancer like lauroylcarnitine.

TABLE 5

Effect of Formulation on the Absorption of Salmon Calcitonin from the Duodenum of the Dog

| | Formulation | Peak Plasma Calcitonin ng/ml | Absolute Bioavailability percent |
|---|---|---|---|
| I. | Calcitonin (25 mg) | 1.15 | 0.015 |
| II. | Citric acid (192 mg) Calcitonin (10 mg) | 10.65 | 0.37 |
| III. | Citric acid (192 mg) Taurodeoxycholic acid (20 mg) Calcitonin (5 mg) | 14.99 | 0.81 |

Method

Modified vascular access ports were surgically implanted into the duodenum, ileum and colon of male beagle dogs. The septum/reservoir bodies of the ports were implanted under the skin and were used as sites for the administration of calcitonin formulations. Before and after the administration of calcitonin formulations into conscious dogs, the ports were flushed with 2 ml of the formulation without calcitonin. Blood (2 ml) was collected through angiocatheter tubes in the leg vein at t=30, 15 and 0 before administration of calcitonin and at 5, 10, 20, 30, 40, 50, 60 and every 15 minutes thereafter for 2 hours. Samples of blood were centrifuged for 10 minutes at 2600 g and the resulting plasma supernatant was stored at $-20°$ C. The concentration of calcitonin in plasma was determined by a competitive radioimmunoassay. The absolute bioavailability (i.e. relative to an intravenous dose of calcitonin) was calculated from the areas under the curve obtained from plots of the plasma concentration as a function of time obtained.

Results and Discussion

The absolute bioavailability of calcitonin administered in water (I) was 0.015%. In the presence of 192 mg citric acid (II) the bioavailability of calcitonin increased 25 fold. The inclusion of 20 mg taurodeoxycholic acid in the formulation (III) produced an additional 2.2 fold increased in absolute bioavailability to 0.81%. The combination of a pH-lowering compound, citric acid, and an enhancer, taurodeoxycholic acid, resulted in overall 54 fold increased in the absolute bioavailability of salmon calcitonin.

Method

Starch and gelatin capsules were filled with the indicated formulations and coated for 60 min with either hydroxypropylmethylcellulose phthalate 50 (I,II,III) (1% weight gain) or Eudragit L 30 D-55 (IV) (10% weight gain) in a pan coater. The stability of the capsules in 0.1N HCl were determined in a dissolution bath using the "basket method." At least 2 dogs were given each of the indicated capsules by mouth and blood was sampled and analyzed for salmon calcitonin as previously described.

Results

The bioavailability of 10 mg calcitonin mixed with 100 mg citric acid and 100 mg taurodeoxycholic acid and delivered in a starch capsule (I) was 0.07%. When the same formulation was given to dogs in a gelatin capsule (II), the bioavailability of salmon calcitonin increased to 0.26%. A six fold increase in the amount of citric acid and a 50% reduction in the amount of calcitonin (III) resulted in a nearly 3 fold increase in calcitonin bioavailability.

When the enteric coat was changed from hydroxypropylmethylcellulose phthalate 50 to Eudragit L 30 D-55, a methacrylate polymer and the formulation was kept the same (IV), the bioavailability of salmon calcitonin increased from 0.62% to 1.48%. Changing the enteric coat from hydroxypropylmethylcellulose phthalate 50 to Eudragit L 30 D-55 resulted in increased stability of the capsule in 0.1N HCl. This increased stability resulted in peak calcitonin levels appearing at a later time point in the dog's blood. The instability of capsules I, II and III in HCl suggests that these capsules were potentially opening in the dogs' stomachs, whereas the improved stability of capsule IV suggests that it was completely stable in the stomachs of dogs and was opening in the intestines of dogs. This indicates that a certain minimum enteric coating amount is preferred. At the same time, too much coating can delay release of calcitonin behind release of other important components (e.g., acid and detergent). Preferably, enteric coating adds 5 to 15% to the weight of the uncoated pharmaceutical.

TABLE 6

Effect of Dosage Form and Formulation on the Absolute Bioavailability of Salmon Calcitonin Administered Orally to Dogs

| | Capsule | Dissolution in HCl min | Formulation | Peak Plasma Calcitonin ng/ml | Peak Plasma Calcitonin min | Absoulte Bioavailability percent |
|---|---|---|---|---|---|---|
| I. | Starch | 10 | Citric acid (100 mg) Taurodeoxycholic acid (100 mg) Calcitonin (10 mg) | 0.98 | 10–30 | 0.07 |
| II. | Gelatin | 30 | Citric acid (100 mg) Taurodeoxycholic acid (100 mg) Calcitonin (10 mg) | 5.79 | 10–30 | 0.26 |
| III. | Gelatin | 30 | Citric acid (600 mg) Taurodeoxycholic acid (80 mg) Calcitonin (5 mg) | 6.92 | 10–30 | 0.62 |
| IV. | Gelatin | >60 | Citric acid (600 mg) Taurodeoxycholic acid (80 mg) Calcitonin (5 mg) | 7.79 | 90 | 1.48 |

TABLE 7

PHARMACOKINETICS OF ORAL CALCITONIN (10.5 mg) IN HUMANS

| Time min | Subject 1 | Subject 2 | Subject 3 | Subject 4 | Subject 5 | Mean |
|---|---|---|---|---|---|---|
| | | | Plasma Calcitonin (pg/ml) | | | |
| 0 | 0 | 0 | 0 | 0 | 0 | 0 |
| 15 | 34 | 0 | 0 | 0 | 1 | 7 |
| 30 | 497 | 91 | 206 | 0 | 70 | 173 |
| 40 | 327 | 86 | 99 | 26 | 35 | 114 |
| 50 | 173 | 114 | 78 | 117 | 26 | 102 |
| 60 | 87 | 106 | 40 | 180 | 20 | 87 |
| 70 | 72 | 108 | 64 | 63 | 35 | 68 |
| 80 | 27 | 85 | 54 | 30 | 25 | 44 |
| 90 | 43 | 102 | 46 | 19 | 14 | 45 |
| 100 | 40 | 89 | 28 | 11 | 28 | 41 |
| 110 | 0 | 91 | 16 | 13 | 0 | 24 |
| 120 | 49 | 117 | 34 | 0 | 6 | 41 |
| 180 | 34 | 107 | 0 | 0 | 16 | 41 |
| Bioavailability (%) | .06 | 0.94 | 0.03 | 0.02 | 0.02 | 0.03 |

Methods

Starch capsules were filled with 138 mg citric acid, 105 mg taurodeoxycholic acid and 10.5 mg salmon calcitonin. The capsules were coated for 20 min with hydroxypropylmethylcellulose phthalate 50 in a pan coater and stored at 4° C. Fasted subjects were given 1 capsule followed by a glass of orange juice in the morning of the study. Samples of blood were taken 15 minutes before taking the capsules and at the indicated times after taking the calcitonin capsule. The concentration of calcitonin in blood was determined by competitive radioimmunoassay. The absolute bioavailability (i.e., relative to an intravenous dose of calcitonin) was calculated from the areas under curve obtained from plots of the plasma concentration of calcitonin as a function of time.

Results

When 10.5 milligrams of salmon calcitonin alone was administered to humans, no detectable serum levels of salmon calcitonin resulted. However, when individuals were given the composition of the invention as described in Table 7, maximum levels of calcitonin were detected in the blood between 30 and 60 minutes after the individuals took the capsule. The maximum concentration of calcitonin in the blood was between 70 and 497 pg/ml. The mean peak concentration of calcitonin for the 5 individuals was 173 pg/ml at t=30 min. The absolute bioavailability ranged from 0.02 to 0.06% with a population mean of 0.03%.

Although the present invention has been described in relation to particular embodiments thereof many other variations and modifications and other uses will become apparent to those skilled in the art. The present invention therefore is not limited by the specific disclosure herein, but only by the appended claims.

What is claimed is:

1. A pharmaceutical composition for oral delivery of salmon calcitonin comprising:
   (A) a therapeutically effective amount of said salmon calcitonin;
   (B) at least one pharmaceutically acceptable pH-lowering agent;
   (C) at least one absorption enhancer effective to promote bioavailability of said salmon calcitonin; and
   (D) an enteric coating;
wherein said pH-lowering agent is present in said pharmaceutical composition in a quantity which, if added to 10 milliliters of 0.1M aqueous sodium bicarbonate solutions would be sufficient to lower the pH of said solution to no higher than 5.5.

2. The pharmaceutical composition of claim 1, wherein said enteric coating is present at a weight which is no more than 20% of the weight of the remainder of said pharmaceutical composition excluding said enteric coating.

3. The pharmaceutical composition of claim 1, wherein said enteric coating is present at a weight which is no more than 5–15% of the weight of the remainder of said pharmaceutical composition excluding said enteric coating.

4. The pharmaceutical composition of claim 1, wherein said absorption enhancer is a surface active agent.

5. The pharmaceutical composition of claim 4, wherein said surface active agent is absorbable or biodegradable.

6. The pharmaceutical composition of claim 5, wherein said surface active agent is selected from the group consisting of acylcarnitines, phospholipids and bile acids.

7. The pharmaceutical composition of claim 1, wherein said absorption enhancer is a surface active agent selected from the group consisting of (i) an anionic agent that is a cholesterol derivative, (ii) a mixture of a negative charge neutralizer and an anionic surface active agent, (iii) nonionic surface active agents, and (iv) cationic surface active agents.

8. The pharmaceutical composition of claim 1, wherein said absorption enhancer is selected from the group consisting of a cationic surfactant and an anionic surfactant that is a cholesterol derivative.

9. The pharmaceutical composition of claim 1, wherein said pharmaceutical composition includes at least two absorption enhancers, one of which is a cationic surface active agent, and another of which is an anionic surface active agent that is a cholesterol derivative.

10. The pharmaceutical composition of claim 9, wherein said anionic surface active agent is an acid-soluble bile acid.

11. The pharmaceutical composition of claim 10, wherein said enteric coating is present at a weight that is no more than 20% of the combined weight of the remainder of said pharmaceutical composition excluding said enteric coating.

12. The pharmaceutical composition of claim 11, wherein all of said absorption enhancers are absorbable or biodegradable.

13. The pharmaceutical composition of claim 7, wherein said enteric coating is present at a weight which is no more than 20% of the combined weight of the remainder of the pharmaceutical composition excluding said enteric coating.

14. The pharmaceutical composition of claim 1, further comprising an amount of a protein effective to reduce non-specific adsorption of said salmon calcitonin.

15. The pharmaceutical composition of claim 14 wherein said protein is albumin, casein, or soy protein.

16. The pharmaceutical composition of claim 1 further comprising a peptide that is susceptible to degradation by intestinal proteases.

17. A method for enhancing the bioavailability of salmon calcitonin delivered orally, said method comprising selectively releasing said salmon calcitonin, together with at least one pH-lowering agent and at least one absorption enhancer, into a patient's intestine following passage of said salmon calcitonin, pH-lowering agent and absorption enhancer through said patient's mouth and stomach under protection of an enteric coating which substantially prevents contact between stomach proteases and said salmon calcitonin;

wherein said pH-lowering agent is released into said intestine in a quantity which, if added to 10 milliliters of 0.1M aqueous sodium bicarbonate solution, would be sufficient to lower pH of said solution to no higher than 5.5.

18. The method of claim 17, wherein said enteric coating is present at a weight which is no more than 20% of the weight of the remainder of all components administered to said patient exclusive said enteric coating.

19. The method of claim 17, wherein said enteric coating is present at a weight which is no more than 5–15% of the weight of the remainder of all components administered to said patient exclusive of said enteric coating.

20. The method of claim 17, wherein said absorption enhancer is a surface active agent.

21. The method of claim 20, wherein said surface active agent is absorbable or biodegradable.

22. The method of claim 21, wherein said surface active agent is selected from the group consisting of acylcarnitines, phospholipids and bile acids.

23. The method of claim 17, wherein said absorption enhancer is a surface active agent selected from the group consisting of (i) an anionic agent that is a cholesterol derivative, (ii) a mixture of a negative charge neutralizer and an anionic surface active agent, (iii) a nonionic surface active agent, and (iv) a cationic surface active agent.

24. The method of claim 17, wherein said absorption enhancer is selected from the group consisting of a cationic surface active agent and an anionic surface active agent that is a cholesterol derivative.

25. The method of claim 24, comprising administering at least two absorption enhancers, one of which is a cationic surface active agent, and another of which is an anionic surface active agent that is a cholesterol derivative.

26. The method of claim 25, wherein said anionic surface active agent is an acid-soluble bile acid.

27. The method of claim 26, wherein said enteric coating is present at a weight that is no more than 20% of the combined weight of all components administered to said patient, exclusive of said enteric coating.

28. The method of claim 27, wherein all absorption enhancers that are administered are absorbable or biodegradable.

29. The method of claim 23, wherein said enteric coating is present at a weight which is no more than 20% of the combined weight of the remainder of all components administered to said patient exclusive of said enteric coating.

30. The method of claim 17, wherein a protein is administered together with said salmon calcitonin in an amount sufficient to reduce non-specific adsorption of said salmon calcitonin.

31. The method of claim 30 wherein said protein is albumin, casein or soy protein.

32. The method of claim 17 further comprising a peptide that is susceptible to degradation by intestinal proteases.

* * * * *